United States Patent
Lombardía et al.

(10) Patent No.: US 11,795,340 B2
(45) Date of Patent: Oct. 24, 2023

(54) COMPOSITON SENSITIVE TO UV-C RADIATION AND UV-C STERILIZATION OR DISINFECTION DOSIMETER

(71) Applicants: TERRAGENE S.A., Alvear (AR); TERRAGENE LLC, Spring, TX (US)

(72) Inventors: Esteban Lombardía, Alvear (AR); Adrián Jesús Rovetto, Alvear (AR)

(73) Assignees: TERRAGENE S.A., Alvear (AR); TERRAGENE LLC, Spring, TX (US)

( * ) Notice: Subject to any disclaimer, the term of this patent is extended or adjusted under 35 U.S.C. 154(b) by 565 days.

(21) Appl. No.: 17/010,458

(22) Filed: Sep. 2, 2020

(65) Prior Publication Data

US 2022/0064468 A1    Mar. 3, 2022

(51) Int. Cl.
| | |
|---|---|
| *C09D 11/50* | (2014.01) |
| *A61L 2/10* | (2006.01) |
| *A61L 2/28* | (2006.01) |
| *B41M 1/12* | (2006.01) |
| *C09D 11/037* | (2014.01) |
| *C09D 11/106* | (2014.01) |

(52) U.S. Cl.
CPC ............... *C09D 11/50* (2013.01); *A61L 2/10* (2013.01); *A61L 2/28* (2013.01); *B41M 1/12* (2013.01); *C09D 11/037* (2013.01); *C09D 11/106* (2013.01)

(58) Field of Classification Search
CPC .... A61L 2/10; A61L 2/28; B41M 1/12; C09D 11/037; C09D 11/106; C09D 11/50
See application file for complete search history.

(56) References Cited

U.S. PATENT DOCUMENTS

| | | | |
|---|---|---|---|
| 2,738,429 A | 3/1956 | Goldblith | |
| 3,226,545 A | * 12/1965 | Potsaid | ............ G01T 1/04 250/473.1 |
| 3,290,499 A | 12/1966 | Vale et al. | |
| 4,136,102 A | 1/1979 | Crivello | |
| 4,161,478 A | 7/1979 | Crivello et al. | |
| 4,219,654 A | 8/1980 | Crivello | |
| 4,407,759 A | 10/1983 | Crivello | |
| 4,417,061 A | 11/1983 | Crivello | |
| 4,829,187 A | 5/1989 | Tomita et al. | |
| 5,028,792 A | 7/1991 | Mullis | |

(Continued)

FOREIGN PATENT DOCUMENTS

| | | |
|---|---|---|
| AU | 2006100303 A4 * | 5/2006 |
| EP | 0389113 A2 | 9/1990 |

(Continued)

OTHER PUBLICATIONS

X. Xiong, Aránzazu del Campo, J. Cui; : Photoresponsive Polymers;Smart Polymers and Their Applications; Chapter 4:, Elsevier 2019; pp. 87-153.

*Primary Examiner* — Sathavaram I Reddy
(74) *Attorney, Agent, or Firm* — Muncy, Geissler, Olds & Lowe, P.C.

(57) ABSTRACT

A reactive ink composition comprising a UV-C radiation sensitive polymer, an acid scavenger, a photoinitiator, and a pH-sensitive dye. A method to print a composition onto a UV-C radiation dosimeter using a "layer-by-layer" deposition technique, as well as a dosimeter comprising the reactive ink composition, useful in monitoring the efficiency of a UV-C radiation sterilization or disinfection process.

16 Claims, 2 Drawing Sheets

(56) References Cited

U.S. PATENT DOCUMENTS

| | | |
|---|---|---|
| 6,437,346 B1 | 8/2002 | Goudjil |
| 6,504,161 B1 | 1/2003 | Jackson et al. |
| 7,589,331 B2 | 9/2009 | Havens et al. |
| 9,097,588 B2 | 8/2015 | Mills et al. |
| 2011/0065203 A1* | 3/2011 | Studer .................... G03C 1/732 |
| | | 436/164 |
| 2020/0149960 A1 | 5/2020 | Foller et al. |

FOREIGN PATENT DOCUMENTS

| | | |
|---|---|---|
| WO | WO-9401503 A1 | 1/1994 |
| WO | WO-2007-001908 A1 | 1/2007 |
| WO | WO-2009-103611 A1 | 8/2009 |
| WO | WO-2010-070920 A1 | 6/2010 |
| WO | WO-2010-112408 A1 | 10/2010 |
| WO | WO-2020-095243 A2 | 5/2020 |

\* cited by examiner

COMPOSITON SENSITIVE TO UV-C RADIATION AND UV-C STERILIZATION OR DISINFECTION DOSIMETER

TECHNICAL FIELD

The present invention generally relates to the field of substances for use as reactive inks and to dosimeters to control UV radiation sterilization or disinfection processes. Specifically, the present invention relates to a composition sensitive to UV-C radiation and to a dosimeter to monitor UV-C radiation sterilization or disinfection processes comprising said composition.

BACKGROUND

Sterilization or disinfection dosimeters or indicators are devices used to monitor the efficiency of a sterilization or disinfection process. These devices, generally in the form of indicator strips, tapes or labels, comprise a reactive compound which may undergo a change in its color or other readily visible property as a result from a physical change or chemical reaction of suitable substances or reagents coated on or embedded in the strip, tape or label. Indicators for monitoring sterilization processes of goods, by means of plasma, spray, fog, steam, chemical vapors or gases are described, e.g. in international patent application published as WO 2020/095243.

Other dosimeters may include substances sensitive to ultraviolet (UV) radiation, in order to monitor the efficiency of a sterilization or disinfection process using UV radiation. UV radiation can be divided into three groups A, B and C according to its wavelength. UV-A comprises wavelengths ranging from 315 to 400 nm, UV-B comprises wavelengths ranging from 280 to 315 nm while UV-C is the portion of the spectrum of wavelengths ranging from 200 to 280 nm. UV-C radiation is known to interact with DNA molecules, thereby inactivating potentially pathogenic microorganisms. Both viruses and bacteria are sensitive to the germicidal effect of UV-C radiation and, for that reason, ultraviolet germicidal irradiation represents an advantageous alternative for sterilization or disinfection processes.

U.S. Pat. No. 4,829,187 discloses an UV radiation reactive ink based on chemical compounds that release acidic compounds that subsequently react with a pH-sensitive dye. U.S. Pat. No. 6,504,161 also discloses an UV radiation reactive ink composition that responds to UV-B radiation and shorter wavelength radiations, based on halogenated adamantine components. Both ink compositions have sensitivities that are difficult to adjust to the UV radiation dose received. In addition, these ink compositions display a disadvantageous reversion to their initial color states.

Patent application US 2020/0149960 discloses a wearable dosimeter that informs users of both their instantaneous and accumulated solar UV radiation exposure, the dosimeter being adapted for detecting UV-A and UV-B radiation.

U.S. Pat. No. 9,097,588 discloses a dosimeter comprising an UV radiation reactive ink. Although this ink may be adapted for UV-C radiation sterilization or disinfection processes, due to its chemical composition, the ink may quickly revert from the color reached after being exposed to UV radiation, to its initial color. This reversion effect is disadvantageous in case the results of the disinfection process efficiency need to be stored or if accumulated radiation doses are to be assessed based on the color change of the dosimeter.

International patent application published as WO 2007/001908 discloses an UV-C radiation sensitive composition comprising a halogenated polymer and an UV radiation sensitive dye. The composition comprises a diluent, based on cellulose derivatives, that helps attenuate its UV radiation sensitivity.

There is therefore a need to provide an ink composition sensitive to UV-C radiation that can provide reliable readings on the efficiency of a UV-C radiation sterilization or disinfection process, having enhanced sensitivity and color stability in a wider range of UV-C radiation doses.

SUMMARY

The present invention allows to overcome the drawbacks of the prior art by providing an UV-C radiation reactive ink composition, a method for printing a reactive ink composition and a dosimeter comprising a reactive ink composition printed onto a suitable substrate. The reactive ink composition of the invention can be included in a dosimeter to monitor the efficiency of a sterilization or disinfection process, such as a sterilization or disinfection process by continuous UV-C or pulsed UV (PX-UV) radiation.

Therefore, a first object of the invention is a composition comprising:
- an UV-C radiation sensitive polymer,
- an acid scavenger,
- a photoinitiator, and
- a pH-sensitive dye.

In a preferred embodiment, the photoinitiator is 9% to 15% in weight of the composition.

In preferred embodiments, the UV-C radiation sensitive polymer is 10% to 30% in weight of the composition.

In other preferred embodiments, the acid scavenger is 0.25% to 0.75% in weight of the composition.

In further preferred embodiments, the pH-sensitive dye is 0.5% to 1.5% in weight of the composition.

In an embodiment, the composition further comprises a radiation screening agent. Preferably, the screening agent is 0.1% to 0.3% in weight of the composition.

In an embodiment, the composition further comprises a background dye. Preferably, the background dye is 0.25% to 0.75% in weight of the composition.

In an embodiment, the composition further comprises a solvent. Preferably, the solvent is 43% to 73% in weight of the composition.

In a preferred embodiment, the composition comprises an UV-C radiation sensitive polymer, an acid scavenger, a photoinitiator, a pH-sensitive dye, a radiation screening agent, a background dye and a solvent. Preferably, the composition consists of an UV-C radiation sensitive polymer, an acid scavenger, a photoinitiator, a pH-sensitive dye, a radiation screening agent, a background dye and a solvent.

In preferred embodiments, the UV-C radiation sensitive polymer is 10% to 30% in weight of the composition, the acid scavenger is 0.25% to 0.75% in weight of the composition, the photoinitiator is 9% to 15% in weight of the composition, the pH-sensitive dye is 0.5% to 1.5% in weight of the composition, the radiation screening agent is 0.1% to 0.3% in weight of the composition, the background dye is 0.25% to 0.75% in weight of the composition and the solvent is 43% to 73% in weight of the composition.

A further object of the invention is a device comprising the composition of the invention, wherein the device comprises:
- a substrate,
- a first layer on top of the substrate, comprising the UV-C radiation sensitive polymer, the photoinitiator, the acid scavenger, the background dye and the pH-sensitive dye, and
- a second layer on top of the first layer comprising the radiation screening agent.

Yet another object of the invention is a method to print a composition onto a substrate, comprising the steps of:
- depositing a first layer on top of the substrate, comprising an UV-C radiation sensitive polymer, a photoinitiator, an acid scavenger, a background dye and a pH-sensitive dye, depositing a second layer on top of the first layer, comprising a radiation screening agent.

In preferred embodiments of said aspects of the invention, the UV-C radiation sensitive polymer is selected from polyurethane, ethylene chlorotrifluoroethylene, polyvinyl chloride, hydroxylated polyvinyl chloride, carboxylated polyvinyl chloride, carboxylated polyethylene, styrene polymers, polyvinylidene chloride, poly(chlorotrifluoroethylene), poly(tetrafluoroethylene), polyethylene, chlorinated poly(vinylidene fluoride), poly(chlorotrifluoroethylene), fluorinated ethylene propylene copolymer, poly(2-chloro-1,3-butadiene) and mixtures or copolymers thereof.

In other preferred embodiments, the acid scavenger is selected from 1,4-diazabicyclo[2.2.2]octane; 2,6-di-tert-butylpyridine; dibutyl 2,6-pyridinedicarboxylate, 1,3-diphenylguanidine; diphenylamine; 2,4-dihydroxy-benzophenone; [5.4.0]undec-7-ene (1,5-5); 1.5-diazabicyclo [4.3.0] non-5-ene, 4-(dimethylamino) pyridine, hexamethylenetetramine and mixtures thereof.

In preferred embodiments, the photoinitiator is selected from α-hydroxyketones, phenylglyoxylate, benzilketal dimeric α-hydroxyketones, phenylglyoxylate, α-aminoketones, acylphosphinoxides, benzophenones, thioxanthones and mixtures thereof. More preferably, the photoinitiator is selected from benzoin methyl ether, 2,2-dimethoxy-2-phenylacetophenone; 2-hydroxy-2-methylphenylpropane-1-one, α-hydroxy-acetophenone; bis(2,6-dimethoxybenzoyl)-2,4,4-trimethylpentylphosphine oxide, 2-hydroxy-2-methyl-1-phenyl-propan-1-one; 2,4,6-trimethylbenzoyldiphenylphosphine oxide, methanesulfonyl chloride, methyl phenyl sulfone, phenyl tribromomethyl sulfone, 4-(trifluoromethoxy)phenyl methyl sulfone, methyl phenyl sulfone, methyl 2,4,5-trichlorophenyl sulfone, chlorobenzyl methyl sulfone, 2,3,5-trichlorophenyl methyl sulfone, 3-amino-4-amino-phenyl methyl sulfone, 2-pyridyl tribromomethyl sulfone, bis(2,6-dichlorobenzoyl)-(4-propylphenyl)-phosphine oxide and mixtures thereof.

In preferred embodiments, the pH-sensitive dye is selected from Alizarine Red, Aniline Blue, Benzopurpurin 4B, Brilliant Green, Bromocresol Purple, Bromophenol Blue, Bromothymol Blue, Clorophenol Red, Congo Red, Cresol Red, Crystal Violet, Erythrosin B, Ethyl Orange, Ethyl Violet, Lisammine Green, Methyl Yellow, 2,4-Dinitrophenol, Methyl Red, Propyl Red, Erytrosin, p-Dimethylaminoazobencene, Methyl Purple, M-Cresol Purple, Bromocresol Green, Solvent Yellow 98, Solvent Yellow 146, Solvent Yellow 56, Azolitmin, 2-(4-Dimethylaminophenylazo)pyridine, Solvent Yellow 21, 4,4'-Bis(4-amino-1-naphthylazo)-2,2'-stilbenedisulfonic acid, Solvent Red 49, Methanil Yellow, 4-Phenylazo-1-naphthylamine, Methyl Green, Methyl Orange, Methyl Red, Methyl Violet 2B, New Fuschin, Oralochite Green Oxalate, Orange IV, Phenol Red, Phenylazoniline, P-Methyl Red, Quinaldine Red, Bromocresol Red, Rezasurin and Thymol Blue and mixtures thereof.

In further preferred embodiments, the composition further comprises a radiation screening agent. Preferably, the screening agent is selected from compounds of the benzotriazole family, compounds of the triazine family, 4-(1,1-dimethylethyl)-4'-methoxydibenzoyl-methane, phorone, menthyl anthranilate, 2-hydroxy-4-methoxybenzophenone, 2,2-dihydroxy-4-methoxybenzophenone and 2-amino-benzophenone, as well as mixtures thereof.

In other preferred embodiments, the composition further comprises a background dye. Preferably, the background dye is selected from Malachite Green oxalate, Crystal Violet, Methyl Violet 2B, Ethyl Violet, new Fuchsin, Victoria Blue B, Victoria Pure Blue BO, Toluidine Blue O, Luxol Brilliant Green BL, Disperse Blue 1, Brilliant Blue R, Victoria Blue R, Quinea Green B, Thionin, Meldolas Blue, Methylene Green, Lissamine Green B, Alkali Blue 6B, Brilliant Green, Spirirt Soluble HLK BASF, Victoria Green S Extra, Acid Violet 17, Eriochrome Black T, Eriochrome Blue Black B, D & C Green No. 2, Spirirt Soluble Fast RR, Spirit Soluble Fast Red 3B, D & C Red No. 22, Nitro Red, Congo Red, Brilliant Cresyl Blue ALD, Arsenazo 1, Basic Red 29, Bismarck Brown R, Methylene Violet, Methylene Violet 3RAX, Mordant Brown 1, Reactive Black 5, Mordant Brown 48, Acid Brown AX987, Acid Violet AX990, Basic Red 15, Mordant Red 19, Bromopyrogallol Red, Brilliant Blue G, Acid Black 24, Patent Blue Violet, Disperse Red 13, Sudan Black B, Janus Green B, Acridine Orange Base, Fast Green FCF, Patent Blue VF, Acid Red 97, Sulforhodamine B, Xylenol Orange Sodium Salt, Azure B, Spirit Soluble Fast Yellow G, Disperse Yellow 3, Keystone Soap Fluoro Green, Calco Oil Blue N, Oil Blue A, Calco Oil Green, D & C Red No. 33, D & C Green No. 5, Bordeaux R, Xylenol Cyanole FF, Crystal Scarlet, Basic Blue 41, Evans Blue, Chicago Sky Blue 6B, Acid Blue 113, Acid Blue 120, Acid Red 88, Acid Red 151, Acid Violet 5, Disperse Red 1, Direct Red 81, Disperse Red 19, Sudan Red 7B, Basic Red 73, Acid Green AX986 and mixtures thereof.

In preferred embodiments, the solvent is selected from acetone, methyl ethyl ketone, cyclopentanone, cyclohexanone, water, and mixtures thereof.

In a preferred embodiment, the UV-C radiation sensitive polymer is hydroxylated polyvinyl chloride, the acid scavenger is 1,4-diazabicyclo[2.2.2]octane, the photoinitiator is tribromomethyl phenyl sulfone and the pH-sensitive dye is Congo Red.

In another preferred embodiment, the UV-C radiation sensitive polymer is polyvinyl chloride, the acid scavenger is hexamethylenetetramine, the photoinitiator is benzoin methyl ether and the pH-sensitive dye is Alizarine Red.

In another preferred embodiment, the UV-C radiation sensitive polymer is polystyrene, the acid scavenger is 2,6-di-tert-butylpyridine, the photoinitiator is α-hydroxyacetophenone and the pH-sensitive dye is Aniline Blue.

In yet another preferred embodiment, the UV-C radiation sensitive polymer is a fluorinated ethylene propylene copolymer, the acid scavenger is diphenylamine, the photoinitiator is 2,4,6-trimethylbenzoyldiphenylphosphine oxide and the pH-sensitive dye is Methyl Green.

In a preferred embodiment, the UV-C radiation sensitive polymer is polyvinyl chloride, the acid scavenger is diphenylamine, the photoinitiator is phenyl tribromomethyl sulfone and the pH-sensitive dye is Solvent Yellow 56. Preferably, the composition further comprises hydroxyphenyl-triazine as a radiation screening agent and Disperse Yellow 3 as a background dye.

DETAILED DESCRIPTION

Figure 1:
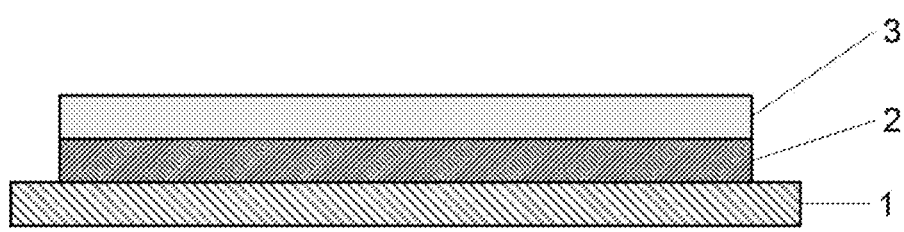
FIG. 1 shows the layered structure of a dosimeter comprising the reactive ink composition of the invention printed onto the substrate with the radiation screening layer printed onto the ink layer.

The invention will be described in further detail below and illustrated by non-limiting examples of specific embodiments.

The present invention provides a reactive ink composition comprising an UV-C radiation sensitive polymer, an acid scavenger, a photoinitiator and a pH-sensitive dye. The invention is adapted for monitoring sterilization or disinfection processes, such as sterilization or disinfection processes employing UV-C radiation at 254 nm, for example provided by a Hg-vapor lamp, or a sterilization processes employing pulsed UV (PX-UV) employing radiation ranging from 200 to 315 nm, for example provided by Xe-vapor lamp.

The UV-C radiation sensitive polymer is a synthetic polymer which can react upon exposure to UV-C radiation, releasing acidic compounds. Non-limiting examples of UV-C radiation sensitive polymers of the reactive ink composition provided by the invention include polyurethane, ethylene chlorotrifluoroethylene, polyvinyl chloride, hydroxylated polyvinyl chloride, carboxylated polyvinyl chloride, carboxylated polyethylene, styrene polymers, polyvinylidene chloride, poly(chlorotrifluoroethylene), poly(tetrafluoroethylene), polyethylene, chlorinated poly(vinylidene fluoride), poly(chlorotrifluoroethylene), fluorinated ethylene propylene copolymer, poly(2-chloro-1,3-butadiene) or other halogenated polymers, as well as mixtures or copolymers thereof. The UV-C radiation sensitive polymer is present in a proportion of about 10% to about 30% in weight of the reactive ink composition.

The acid scavenger affects the UV-C radiation dose to which the reactive ink composition will react to, by regulating the concentration of acidic compounds generated by degradation of the UV-C radiation sensitive polymer. Non-limiting examples of acid scavengers of the reactive ink composition provided by the invention include 1,4-diazabicyclo[2.2.2]octane; 2,6-di-tert-butylpyridine; dibutyl 2,6-pyridinedicarboxylate, 1,3-diphenylguanidine; diphenylamine; 2,4-dihydroxy-benzophenone; [5.4.0]undec-7-ene (1,5-5); 1.5-diazabicyclo [4.3.0]non-5-ene and 4-(dimethylamino) pyridine, hexamethylenetetramine, as well as mixtures thereof. Advantageously, the acid scavenger is present in a proportion of about 0.25% to about 0.75% in weight of the reactive ink composition.

The photoinitiator triggers the degradation reaction of the UV-C radiation sensitive polymer, thereby causing the release of acidic compounds. In addition, the reaction is advantageously rendered irreversible, thereby precluding reversion of the result shown by the dosimeter, which provides a more reliable and stable reading on the efficiency of a UV-C radiation disinfection or sterilization process. The photoinitiator is different from the acid scavenger. Non-limiting examples of the photoinitiator of the reactive ink composition provided by the invention include α-hydroxyketones, phenylglyoxylate, benzilketal dimeric α-hydroxyketones, phenylglyoxylate, α-aminoketones, acylphosphinoxides, thioxanthones and other compounds comprising an halogenmethylsulfonyl moiety, as well as mixtures thereof. More particularly, non-limiting examples of the photoinitiator of the reactive ink composition provided by the invention include benzoin methyl ether, 2,2-dimethoxy-2-phenylacetophenone; 2-hydroxy-2-methylphenylpropane-1-one, α-hydroxy-acetophenone; bis(2,6-dimethoxybenzoyl)-2,4,4-trimethylpentylphosphine oxide, 2-hydroxy-2-methyl-1-phenyl-propan-1-one; 2,4,6-trimethylbenzoyldiphenylphosphine oxide, methanesulfonyl chloride, methyl phenyl sulfone, phenyl tribromomethyl sulfone, 4-(trifluoromethoxy)phenyl methyl sulfone, methyl phenyl sulfone, methyl 2,4,5-trichlorophenyl sulfone, chlorobenzyl methyl sulfone, 2,3,5-trichlorophenyl methyl sulfone, 3-amino-4-amino-phenyl methyl sulfone, 2-pyridyl tribromomethyl sulfone, bis(2,6-dichlorobenzoyl)-(4-propylphenyl)-phosphine oxide, as well as mixtures thereof. Advantageously, the photoinitiator is present in a proportion of about 9% to about 15% in weight of the reactive ink composition.

The pH-sensitive dye is a substance that changes its color when exposed to an acidic medium. Non-limiting examples of the pH-sensitive dye of the reactive ink composition provided by the invention include Alizarine Red, Aniline Blue, Benzopurpurin 4B, Brilliant Green, Bromocresol Purple, Bromophenol Blue, Bromothymol Blue, Clorophenol Red, Congo Red, Cresol Red, Crystal Violet, Erythrosin B, Ethyl Orange, Ethyl Violet, Lisammine Green, Methyl Yellow, 2,4-Dinitrophenol, Methyl Red, Propyl Red, Erytrosin, p-Dimethylaminoazobencene, Methyl Purple, M-Cresol Purple, Bromocresol Green, Solvent Yellow 98, Solvent Yellow 146, Solvent Yellow 56, Azolitmin, 2-(4-Dimethylaminophenylazo)pyridine, Solvent Yellow 21, 4,4'-Bis(4-amino-1-naphthylazo)-2,2'-stilbenedisulfonic acid, Solvent Red 49, Methanil Yellow, 4-Phenylazo-1-naphthylamine, Methyl Green, Methyl Orange, Methyl Red, Methyl Violet 2B, New Fuschsin, Oralochite Green Oxalate, Orange IV, Phenol Red, Phenylazoniline, P-Methyl Red, Quinaldine Red, Bromocresol Red, Rezasurin and Thymol Blue, as well as mixtures thereof. The pH-sensitive dye is present in a proportion of about 0.5% to about 1.5% in weight of the reactive ink composition.

The reactive ink composition of the invention may also comprise light absorbers reactants or "radiation screening agents", in case the photoinitiator is sensitive to wavelengths other than UV-C. Non-limiting examples of the radiation screening agent of the reactive ink composition provided by the invention include compounds of the benzotriazole family, compounds of the triazine family, 4-(1,1-dimethylethyl)-4'-methoxydibenzoyl-methane, phorone, menthyl anthranilate, 2-hydroxy-4-methoxybenzophenone, 2,2-dihydroxy-4-methoxybenzophenone and 2-amino-benzophenone, as well as mixtures thereof. The radiation screening agent is present in a proportion of about 0.1% to about 0.3% in weight of the reactive ink composition.

In order for the colors shown by the dosimeter comprising the reactive ink composition of the invention to be clearly interpretable to the human eye, a non-reactive coloring compound or "background dye" may be included. Non-limiting examples of the background dye of the reactive ink composition provided by the invention include Malachite Green oxalate, Crystal Violet, Methyl Violet 2B, Ethyl Violet, new Fuchsin, Victoria Blue B, Victoria Pure Blue BO, Toluidine Blue O, Luxol Brilliant Green BL, Disperse Blue 1, Brilliant Blue R, Victoria Blue R, Quinea Green B, Thionin, Meldolas Blue, Methylene Green, Lissamine Green B, Alkali Blue 6B, Brilliant Green, Spirirt Soluble HLK BASF, Victoria Green S Extra, Acid Violet 17, Eriochrome Black T, Eriochrome Blue Black B, D & C Green No. 2, Spirirt Soluble Fast RR, Spirit Soluble Fast Red 3B, D & C Red No. 22, Nitro Red, Congo Red, Brilliant Cresyl Blue ALD, Arsenazo 1, Basic Red 29, Bismarck Brown R, Methylene Violet, Methylene Violet 3RAX, Mordant Brown 1, Reactive Black 5, Mordant Brown 48, Acid Brown AX987, Acid Violet AX990, Basic Red 15, Mordant Red 19, Bromopyrogallol Red, Brilliant Blue G, Acid Black 24, Patent Blue Violet, Disperse Red 13, Sudan Black B, Janus Green B, Acridine Orange Base, Fast Green FCF, Patent Blue VF, Acid Red 97, Sulforhodamine B, Xylenol Orange Sodium Salt, Azure B, Spirit Soluble Fast Yellow G, Disperse Yellow 3, Keystone Soap Fluoro Green, Calco Oil Blue N, Oil Blue A, Calco Oil Green, D & C Red No. 33, D & C Green No. 5, Bordeaux R, Xylenol Cyanole FF, Crystal Scarlet, Basic Blue 41, Evans Blue, Chicago Sky Blue 6B, Acid Blue 113, Acid Blue 120, Acid Red 88, Acid Red 151, Acid Violet 5, Disperse Red 1, Direct Red 81, Disperse Red 19, Sudan Red 7B, Basic Red 73, Acid Green AX986, as well as mixtures thereof. The background dye is present in a proportion of about 0.25% to about 0.75% in weight of the reactive ink composition.

The ink composition may further include a solvent, such as acetone, methyl ethyl ketone, cyclopentanone, cyclohexanone, water, and mixtures thereof. The solvent is about is 43% to about 73% in weight of the composition.

By combining the different components of the composition of the invention, different reactive ink compositions can be obtained to monitor UV-C radiation sterilization or disinfection processes employing UV-C radiation doses ranging from 1 mJ/cm$^2$ to 1500 mJ/cm$^2$, preferably ranging from 10 mJ/cm$^2$ to 1000 mJ/cm$^2$ and even more preferably ranging from 25 mJ/cm$^2$ to 250 mJ/cm$^2$.

The invention further provides a dosimeter, obtained by the deposition of a first layer of the reactive ink composition onto a substrate and a second radiation screening layer onto the ink layer.

In order to prepare the dosimeter of the invention, the reactive ink composition is printed onto a substrate or support. The printing is carried out using a "layer-by-layer" deposition technique, in order to obtain a selective filtering effect, as will be described in further detail below.

Since several of the components of the reactive ink composition may also react to radiation having of different wavelengths the one employed in the sterilization or disinfection process, it is desirable to neutralize the effect of such radiation. To this end, the dosimeter of the invention can be advantageously printed with the reactive ink composition as shown in FIG. 1, such that two layers are deposited onto the substrate or support (1):
  a first layer or bottom layer (2), comprising the UV-C radiation sensitive polymer, the photoinitiator, the acid scavenger, the background dye and the pH-sensitive dye, and
  a second layer or top layer (3), comprising the radiation screening agent for UV-A, UV-B and/or visible radiation.

With this layered arrangement, the bottom layer of the dosimeter of the invention is made reactive to UV-C radiation only.

The substrate or support is generally made from a flexible material, for example, cellulose derivatives, such as paper or cardboard, thermoplastics such as polyethylene, polypropylene, poly(methyl methacrylate) or copolymers thereof, and the like.

The layer-by-layer print of the reactive ink composition is achieved by techniques such as flexographic or silk screen printing.

In the silk screen printing process, a substrate such as a layer of oriented polypropylene (PP) is threaded using commercially available equipment comprising a drying oven, setting the drying temperature to a value between 90 and 120° C. A screen mesh, mesh 60 to 150, is then placed on a frame, at a height of about 1 to 12 mm above the substrate. A minimum of 500 g of a composition comprising a UV-C radiation sensitive polymer, a photoinitiator, an acid scavenger, a background dye and a pH-sensitive dye is loaded into a reservoir and printing onto the substrate is achieved by strokes using a flat blade or squeegee. After about one hundred strokes, an additional 100 g of the composition is loaded into the equipment. After about 1500 strokes, the obtained first layer is removed from the frame. For applying the second layer, this printing process is repeated using a composition comprising a radiation screening agent, optionally comprising a non-reactive polymer, to provide the second layer with increased structural integrity. The drying system ensures that the composition is dried before a second layer is applied over the first layer. It was found that the specific amounts of components are related to the efficiency of this drying process, with higher polymer concentrations interfering with an adequate drying.

In the flexographic process, an anilox roller cylinder with anilox 60-360 and a plate cylinder are used to print a composition comprising a UV-C radiation sensitive polymer, a photoinitiator, an acid scavenger, a background dye and a pH-sensitive dye onto a threaded substrate. In this process, a minimum of 2 kg of composition should be loaded into the equipment tray, with a drying oven temperature between 90 and 120° C. For applying the second layer, this printing process is repeated using a composition comprising a radiation screening agent, optionally comprising a non-reactive polymer, to provide the second layer with increased structural integrity, such as an acrylic polymer. The drying system ensures that the composition is dried before a second layer is applied over the first layer. It was found that the specific amounts of components are related to the efficiency of this drying process, with higher polymer concentrations interfering with an adequate drying.

Several configurations for the dosimeter can be obtained by modifying the substrate or support, particularly its shape and spatial configuration.

Figure 2:
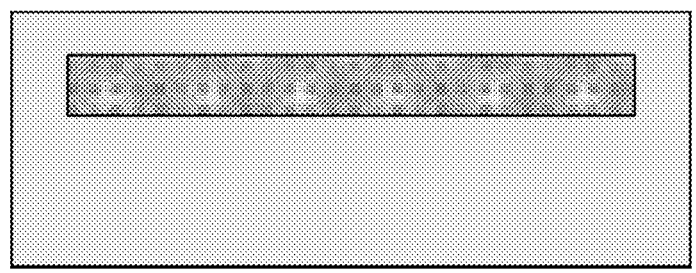
FIG. 2 shows a sterilization or disinfection dosimeter of the invention comprising an indicator stripe.
Figure 3:
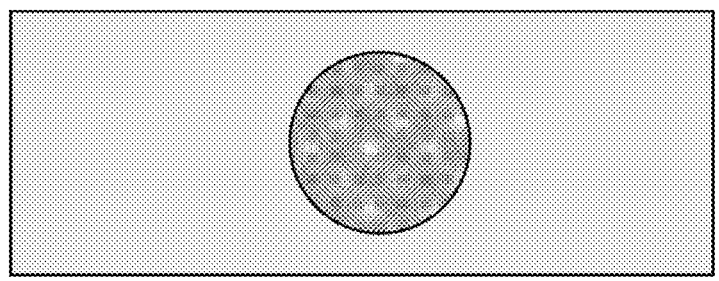
FIG. 3 shows a sterilization or disinfection dosimeter of the invention comprising an indicator disk.

The dosimeter can be configured as indicator strips as shown in FIG. 2, as self-adhesive labels or as round stickers as shown in FIG. 3, or as a three-dimensional object, such as a polyhedron, a pyramid, a tetrahedron, a cube, an octahedron, etc., wherein the reactive ink composition of the invention has been printed into stripes, spots, areas, etc.

In a specific embodiment, the dosimeter is a pyramid having an approximate height of 10.5 cm and an approximate base of 9.0 cm.

The sides of the pyramid are provided with a plurality of stripes comprising the reactive ink composition of the invention. These stripes provide a visible color change indicative of the efficiency of the UV-C radiation disinfection or sterilization process.

Figure 4:
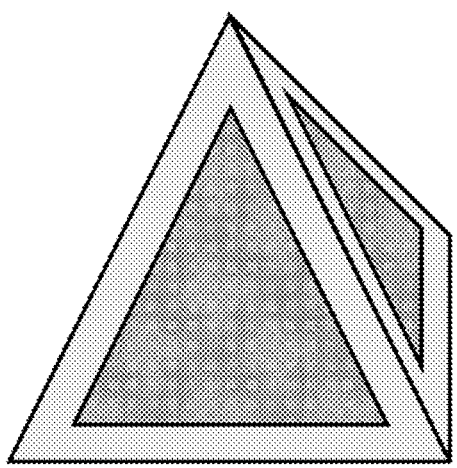
FIG. 4 shows a sterilization or disinfection dosimeter of the invention shaped as a pyramid provided with printed indicator surfaces.

Alternatively, the sides of the pyramid are provided with a region comprising the reactive ink composition of the invention, such as shown in FIG. 4.

The dosimeter can be further provided with suspending means for suspending or hanging the dosimeter in the room to be disinfected or sterilized, such as hangers, hooks, ropes, etc. The desired position of the dosimeter in the room to be disinfected or sterilized can be determined based on the average volume of the room and the particularities of the disinfection or sterilization process to be applied therein. For example, for a UV-C radiation disinfection process in a large room employing a point source of UV-C radiation at 254 nm or pulsed UV (PX-UV) radiation ranging from 200 to 315 nm, the dosimeter may be located, i.e. hanged from the ceiling, in a position far away from the point source, in order to provide a representative and reliable reading on the efficiency of the sterilization or disinfection process, such as in a corner opposite to the point source.

The dosimeter may be configured as a disk or dot, by providing the reactive ink composition printed onto a self-adhesive substrate or support. In a specific embodiment, the disks have a diameter of approximately 15 mm. A plurality of these disks can be adhered to the surfaces of a room to be disinfected or sterilized. The desired position of each of these disks and the number thereof in the room to be disinfected or sterilized can be determined based on the average volume of the room and the particularities of the disinfection or sterilization process to be applied therein. For example, for a UV-C radiation disinfection process in a large room employing a point source of UV-C radiation at 254 nm or pulsed UV (PX-UV) radiation ranging from 200 to 315 nm, between 10 and 20 disks may be adhered to different surfaces of the room at locations far away from the point source, in order to provide a representative and reliable reading on the efficiency of the disinfection process.

EXAMPLES

Reactive ink compositions were prepared in a 500 mL vessel. The components were mixed by means of a disperser, HIMS200 provided by Harrison's Pharma Machinery Pvt. Ltd., at a speed of 3000 rpm for one hour.

The increase on the temperature of the mixture due to the increase on the kinetic energy of the molecules of the components caused by the high speed of the dispersion process, can cause the temperature to reach values as high as 80° C. Temperatures higher than 80° C. can cause the UV-C radiation sensitive polymer reactivity to be affected. The temperature was strictly controlled throughout the dispersion process in order to avoid exceeding 80° C. Each time the temperature reached the threshold value, the dispersion process was stopped until temperature decreased by at least 30° C. and resumed thereafter. Dispersion time was one hour, without counting the dead-times of the stops.

Different reactive ink compositions were prepared, having compositions as described in the following examples.

The reactive ink compositions were printed with flexographic printing machines, such as DBRY320-5C—provided by Shanghai Duxia Industry and Trade Co., Ltd., using anilox 120 or by silk screen printing machines, such as WQ-320 provided by Weigang, using 60-165 mesh, onto oriented polypropylene.

A second layer, an overprint varnish comprising the solvent mixture and radiation screening agent, as well as a non-reactive acrylic polymer for structural integrity, was applied in the same way.

The printed reactive ink compositions were exposed to increasing doses of UV-C radiation in a specially built equipment. The equipment comprises a stainless-steel cabinet of 120 cm (h)×40 cm (w)×40 cm (d) housing a 4 W Phillips continuous UV-C lamp with adjustable height settings (0 to 100 cm from dosimeter), as a source of UV-C radiation at 254 nm. Radiation doses ranging from 0 to 1500 mJ/cm$^2$ were applied to the printed ink compositions samples by exposing them for a period ranging from 5 to 15 minutes to the UV-C radiation source of the equipment, with the samples at a distance ranging from 0 to 100 cm from the source. A visual color change was assessed for every reactive ink composition.

The examples below show that the reactive ink composition of the invention allows fine-tuning the response to a radiation dose, as well as providing a more stable and reliable reading, while also having specific reactivity to UV-C radiation.

Example 1

This composition was used to evaluate the reactivity and effect of every component.

TABLE 1

| Reactive ink composition for Example 1 | | |
|---|---|---|
| Component | Compound | Mass (g) |
| UV-C sensitive polymer | HPVC | 19.14 |
| Solvent | cyclohexanone | 67.46 |
| pH-sensitive dye | Thymol Blue | 0.96 |
| Radiation screening agent | hydroxyphenyl-triazine | 0.15 |
| Photoinitiator | α-hydroxyacetophenone | 11.4 |
| Acid scavenger | diphenylamine | 0.48 |
| Background dye | Disperse yellow 3 | 0.5 |

At a radiation dose of 50 mJ/cm$^2$, the composition started turning from yellow to orange/red.

Example 2

This comparative example was carried out to assess the effect of the photoinitiator in the stability against the reversion of the final color reached by the dosimeter.

TABLE 2

| Reactive ink composition for Example 2 | | |
|---|---|---|
| Component | Compound | Mass (g) |
| UV-C sensitive polymer | HPVC | 19.14 |
| Solvent | cyclohexanone | 67.46 |
| pH-sensitive dye | Thymol Blue | 0.96 |
| Radiation-screening agent | hydroxyphenyl-triazine | 0.15 |
| Photoinitiator | α-hydroxyacetophenone | 9 |
| (Acid scavenger | diphenylamine | 0.48 |
| Background dye | Disperse yellow 3 | 0.5 |

This composition turned from yellow to orange/red only when exposed to a radiation dose of 100 mJ/cm$^2$, indicating the importance of the photoinitiator in the composition in making the ink more reactive to UV-C radiation. It was observed that this composition is more prone to reversion after prolonged storage periods, i. e. over 60 days, indicating a lower stability of the readings.

Example 3

This comparative example was carried out to assess the effect of lower photoinitiator concentrations in the reactivity of the ink.

TABLE 3

Reactive ink composition for Example 3

| Component | Compound | Mass (g) |
|---|---|---|
| UV-C sensitive polymer | HPVC | 19.14 |
| Solvent | cyclohexanone | 67.46 |
| pH-sensitive dye | Thymol Blue | 0.96 |
| Radiation screening agent | hydroxyphenyl-triazine | 0.15 |
| Photoinitiator | α-hydroxyacetophenone | 5.4 |
| Acid scavenger | diphenylamine | 0.48 |
| Background dye | Disperse yellow 3 | 0.5 |

This composition was not able to react to UV-C light unless long exposure times were used. Non-uniform color changes were observed.

Example 4

TABLE 4

Reactive ink composition for Example 4

| Component | Compound | Mass (g) |
|---|---|---|
| UV-C sensitive polymer | HPVC | 19.14 |
| Solvent | cyclohexanone | 67.46 |
| pH-sensitive dye | Thymol Blue | 0.96 |
| Radiation screening agent | hydroxyphenyl-triazine | 0.15 |
| Photoinitiator | α-hydroxyacetophenone | 15.22 |
| Acid scavenger | diphenylamine | 0.48 |
| Background dye | Disperse yellow 3 | 0.5 |

By increasing the amount of photoinitiator, enhanced reactivity of the ink without affecting the long-term stability was obtained. In this case, the composition was reactive to a dose of 25 mJ/cm$^2$, demonstrating the importance of this component. However, for higher photoinitiator concentrations the ink composition was found to be insoluble.

Example 5

TABLE 5

Reactive ink composition for Example 5

| Component | Compound | Mass (g) |
|---|---|---|
| UV-C sensitive polymer | polyvinyl chloride | 20 |
| Solvent | cyclohexanone | 58 |
| pH-sensitive dye | Thymol Blue | 1 |
| Radiation screening agent | hydroxyphenyl-triazine | 0.15 |
| Photoinitiator | phenyl tribromomethyl sulfone | 12 |
| Acid scavenger | 1,3-diphenylguanidine | 0.5 |
| Background dye | Disperse yellow 3 | 0.5 |

This composition was reactive to a radiation dose of 50 mJ/cm$^2$, turning from yellow to orange/red, similarly to the ink composition of Example 1.

Example 6

TABLE 6

Reactive ink composition for Example 6

| Component | Compound | Mass (g) |
|---|---|---|
| UV-C sensitive polymer | polyvinyl chloride | 20 |
| Solvent | cyclohexanone | 58 |
| pH-sensitive dye | Thymol Blue | 1 |
| Radiation screening agent | hydroxyphenyl-triazine | 0.15 |
| Photoinitiator | phenyl tribromomethyl sulfone | 12 |
| Acid scavenger | 1,3-diphenylguanidine | 0.25 |
| Background dye | Disperse yellow 3 | 0.5 |

This composition has an adjusted reactivity, obtained by modifying the amount of acid scavenger.

A radiation dose of 25 mJ/cm$^2$ was enough to generate a visible color change from yellow to orange/red. With the composition, it was observed that minimum changes on the acidity of the substrate onto which the composition is printed, yielded slight color changes. Without being bound by theory, these variations can be attributed to a low acid scavenger concentration.

Example 7

TABLE 7

Reactive ink composition for Example 7

| Component | Compound | Mass (g) |
|---|---|---|
| UV-C sensitive polymer | polyvinyl chloride | 20 |
| Solvent | cyclohexanone | 58 |
| pH-sensitive dye | Thymol Blue | 1 |
| Radiation screening agent | hydroxyphenyl-triazine | 0.15 |
| Photoinitiator | phenyl tribromomethyl sulfone | 12 |
| Acid scavenger | 1,3-diphenylguanidine | 0.75 |
| Background dye | Disperse yellow 3 | 0.5 |

Surprisingly, using higher concentrations of acid scavenger yielded a much "harder" ink composition. A radiation dose of 1500 mJ/cm$^2$ was necessary for the ink composition to change color from yellow to orange/red.

The ink compositions from Examples 5, 6 and 7 have adjusted reactivity without affecting the stability of the ink, because photoinitiator levels were not altered.

Example 8

This comparative example was carried out to assess the effect of polymer content in the reactivity of the ink composition.

TABLE 8

Reactive ink composition for Example 8

| Component | Compound | Mass (g) |
|---|---|---|
| UV-C sensitive polymer | HPVC | 9.14 |
| Solvent | cyclohexanone | 67.46 |
| pH-sensitive dye | Thymol Blue | 0.96 |
| Radiation screening agent | hydroxyphenyl-triazine | 0.15 |
| Photoinitiator | α-hydroxyacetophenone | 11.4 |
| Acid scavenger | diphenylamine | 0.48 |
| Background dye | Disperse yellow 3 | 0.5 |

This concentration reacted to 250 mJ/cm$^2$, but the viscosity of the ink was at a lower limit, resulting in difficulties during the printing process.

Example 9

This comparative example shows the importance of polymer content.

TABLE 9

Reactive ink composition for Example 9

| Component | Compound | Mass (g) |
|---|---|---|
| UV-C sensitive polymer | HPVC | 35 |
| Solvent | cyclohexanone | 67.46 |
| pH-sensitive dye | Thymol Blue | 0.96 |
| Radiation screening agent | hydroxyphenyl-triazine | 0.15 |
| Photoinitiator | α-hydroxyacetophenone | 11.4 |
| Acid scavenger | diphenylamine | 0.48 |
| Background dye | Disperse yellow 3 | 0.5 |

When the composition comprises more than 35% polymer, drying of the ink composition in the productive line was not possible.

Example 10

TABLE 10

Reactive ink composition for Example 10

| Component | Compound | Mass (g) |
|---|---|---|
| UV-C sensitive polymer | HPVC | 19.14 |
| Solvent | cyclohexanone | 67.46 |
| pH-sensitive dye | Thymol Blue | 0.96 |
| Radiation screening agent | hydroxyphenyl-triazine | 0.08 |
| Photoinitiator | α-hydroxyacetophenone | 11.4 |
| Acid scavenger | diphenylamine | 0.48 |
| Background dye | Disperse yellow 3 | 0.5 |

This ink composition reacted similarly to the composition of Example 1, but also reacted to ambient light. When no radiation screening agent is used or a low concentration of radiation screening agent is used, the ink composition was observed to react to different wavelengths, leaving the reactive ink to ambient light, therefore causing a non-specific reaction. Concentrations of radiation screening agents higher than 0.3% did not result in any additional effect.

It is also to be understood that the above description is intended to be illustrative and not restrictive. Many embodiments will be apparent to those of in the art upon reviewing the above description. The scope of the invention should, therefore, be determined not with reference to the above description, but should instead be determined with reference to the appended claims, along with the full scope of equivalents to which such claims are entitled.

Those skilled in the art will recognize or be able to ascertain using no more than routine experimentation, many equivalents to the specific embodiments of the invention described herein. Such equivalents are intended to be encompassed by the appended claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A composition comprising:
   a UV-C radiation sensitive polymer,
   an acid scavenger,
   a photoinitiator, and
   a pH-sensitive dye,
   wherein the photoinitiator is 9% to 15% by weight of the composition, and
   wherein the acid scavenger is 0.25% to 0.75% by weight of the composition and the UV-C radiation sensitive polymer is 10% to 30% by weight of the composition.

2. The composition of claim 1, wherein the photoinitiator is selected from α-hydroxyketones, phenylglyoxylate, benzilketal dimeric α-hydroxyketones, α-aminoketones, acylphosphinoxides, thioxanthones and mixtures thereof.

3. The composition of claim 1, wherein the photoinitiator is selected from benzoin methyl ether, 2,2-dimethoxy-2-phenylacetophenone; 2-hydroxy-2-methylphenylpropane-1-one, α-hydroxy-acetophenone; bis(2,6-dimethoxybenzoyl)-2,4,4-trimethylpentylphosphine oxide, 2-hydroxy-2-methyl-1-phenyl-propan-1-one; 2,4,6-trimethylbenzoyldiphenylphosphine oxide, methanesulfonyl chloride, methyl phenyl sulfone, phenyl tribromomethyl sulfone, 4-(trifluoromethoxy)phenyl methyl sulfone, methyl phenyl sulfone, methyl 2,4,5-trichlorophenyl sulfone, chlorobenzyl methyl sulfone, 2,3,5-trichlorophenyl methyl sulfone, 3-amino-4-amino-phenyl methyl sulfone, 2-pyridyl tribromomethyl sulfone, bis(2,6-dichlorobenzoyl)-(4-propylphenyl)-phosphine oxide and mixtures thereof.

4. The composition of claim 1, wherein the acid scavenger is selected from 1,4-diazabicyclo[2.2.2]octane; 2,6-di-tert-butylpyridine; dibutyl 2,6-pyridinedicarboxylate, 1,3-diphenylguanidine; diphenylamine; 2,4-dihydroxy-benzophenone; [5.4.0]undec-7-ene (1,5-5); 1.5-diazabicyclo [4.3.0] non-5-ene, 4-(dimethylamino) pyridine, hexamethylenetetramine and mixtures thereof.

5. The composition of claim 4, wherein the UV-C radiation sensitive polymer is selected from polyurethane, ethylene chlorotrifluoroethylene, polyvinyl chloride, hydroxylated polyvinyl chloride, carboxylated polyvinyl chloride, carboxylated polyethylene, styrene polymers, polyvinylidene chloride, poly(chlorotrifluoroethylene), poly(tetrafluoroethylene), polyethylene, chlorinated poly(vinylidene fluoride), fluorinated ethylene propylene copolymer, poly(2-chloro-1,3-butadiene) and mixtures or copolymers thereof.

6. The composition of claim 1, further comprising a radiation screening agent.

7. The composition of claim 6, wherein the radiation screening agent is 0.1% to 0.3% by weight of the composition.

8. The composition of claim 6, wherein the radiation screening agent is selected from compounds of the benzotriazole family, compounds of the triazine family, 4-(1,1-dimethylethyl)-4'-methoxydibenzoyl-methane, phorone, menthyl anthranilate, 2-hydroxy-4-methoxybenzophenone, 2,2-dihydroxy-4-methoxybenzophenone and 2-amino-benzophenone and mixtures thereof.

9. The composition of claim 1, wherein the pH-sensitive dye is selected from Alizarine Red, Aniline Blue, Benzopurpurin 4B, Brilliant Green, Bromocresol Purple, Bromophenol Blue, Bromothymol Blue, Clorophenol Red, Congo Red, Cresol Red, Crystal Violet, Erythrosin B, Ethyl Orange, Ethyl Violet, Lisammine Green, Methyl Yellow, 2,4-Dinitrophenol, Methyl Red, Propyl Red, Erytrosin, p-Dimethylaminoazobencene, Methyl Purple, M-Cresol Purple, Bromocresol Green, Solvent Yellow 98, Solvent Yellow 146, Solvent Yellow 56, Azolitmin, 2-(4-Dimethylaminophenylazo)pyridine, Solvent Yellow 21, 4,4'-Bis(4-amino-1-naphthylazo)-2,2'-stilbenedisulfonic acid, Solvent Red 49, Methanil Yellow, 4-Phenylazo-1-naphthylamine, Methyl Green, Methyl Orange, Methyl Red, Methyl Violet 2B, New Fuschsin, Oralochite Green Oxalate, Orange IV, Phenol Red, Phenylazoniline, P-Methyl Red, Quinaldine Red, Bromocresol Red, Rezasurin and Thymol Blue and mixtures thereof.

10. The composition of claim 6, further comprising a background dye.

11. The composition of claim 10, wherein the UV-C radiation sensitive polymer is polyvinyl chloride, the acid scavenger is diphenylamine, the photoinitiator is phenyl tribromomethyl sulfone, the pH-sensitive dye is Solvent Yellow 56, the radiation screening agent is hydroxyphenyltriazine and the background dye is Disperse Yellow 3.

12. A composition comprising:
   a UV-C radiation sensitive polymer;
   an acid scavenger;
   a photoinitiator; and
   a pH-sensitive dye,
   wherein the photoinitiator is 9% to 15% by weight of the composition, the acid scavenger is 0.25% to 0.75% by weight of the composition, and
   wherein the UV-C radiation sensitive polymer is hydroxylated polyvinyl chloride, the acid scavenger is 1,4-diazabicyclo[2.2.2]octane, the photoinitiator is tribromomethyl phenyl sulfone and the pH-sensitive dye is Congo Red.

13. A composition comprising:
   a UV-C radiation sensitive polymer;
   an acid scavenger;
   a photoinitiator; and
   a pH-sensitive dye,
   wherein the photoinitiator is 9% to 15% by weight of the composition, the acid scavenger is 0.25% to 0.75% by weight of the composition, and
   wherein the UV-C radiation sensitive polymer is polyvinyl chloride, the acid scavenger is hexamethylenetetramine, the photoinitiator is benzoin methyl ether and the pH-sensitive dye is Alizarine Red.

14. A device comprising the composition of claim 6, wherein the device comprises:
   a substrate,
   a first layer on top of the substrate, comprising the UV-C radiation sensitive polymer, the photoinitiator, the acid scavenger, the background dye and the pH-sensitive dye, and
   a second layer on top of the first layer, comprising the radiation screening agent.

15. A device comprising the composition of claim 12, wherein the device comprises:
   a substrate;
   a first layer on top of the substrate, comprising the UV-C radiation sensitive polymer, the photoinitiator, the acid scavenger, a background dye and the pH-sensitive dye; and
   a second layer on top of the first layer, comprising a radiation screening agent.

16. A device comprising the composition of claim 13, wherein the device comprises:
   a substrate;
   a first layer on top of the substrate, comprising the UV-C radiation sensitive polymer, the photoinitiator, the acid scavenger, a background dye and the pH-sensitive dye; and
   a second layer on top of the first layer, comprising a radiation screening agent.

* * * * *